Figure 1:
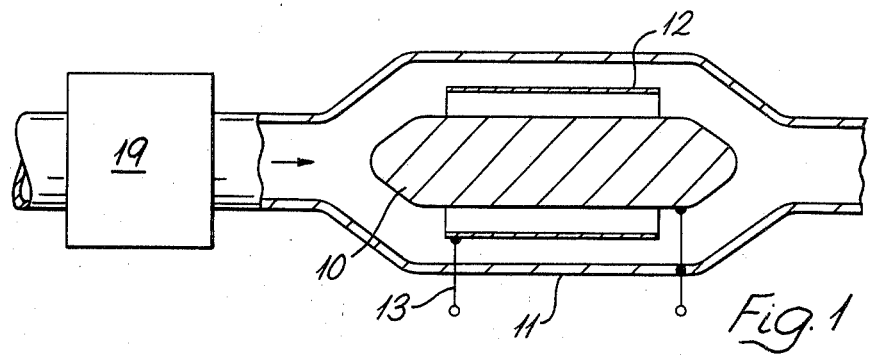

United States Patent [19]

El-Menshawy et al.

[11] 4,392,110
[45] Jul. 5, 1983

[54] METHODS AND APPARATUS FOR MONITORING THE CONDITION OF DIELECTRIC LIQUID IN ELECTRIC DISCHARGE MACHINING

[75] Inventors: Mohamed F. El-Menshawy, Birmingham; Peter A. Woodrow, Sevenoaks; Sushantha K. Bhattacharyya, Birmingham, all of England

[73] Assignee: National Research Development Corporation, London, England

[21] Appl. No.: 158,813

[22] Filed: Jun. 12, 1980

[30] Foreign Application Priority Data

Jun. 12, 1979 [GB] United Kingdom ............... 7920444

[51] Int. Cl.$^3$ .............................................. G01N 27/60
[52] U.S. Cl. .................................. 324/453; 324/204; 324/448; 324/71.4
[58] Field of Search ........... 324/446, 448, 204, 71 CP; 204/129.2, 129.25

[56] References Cited

U.S. PATENT DOCUMENTS

| | | |
|---|---|---|
| 1,807,821 | 6/1931 | Behr .................................... 324/448 |
| 3,233,173 | 2/1966 | Lees et al. ........................... 324/204 |
| 3,440,156 | 4/1969 | Dickson ......................... 204/129.25 |
| 3,916,300 | 10/1975 | Chisdes ............................. 324/448 |
| 4,030,028 | 6/1977 | Allender . | |
| 4,070,660 | 1/1978 | Tauber . | |
| 4,072,892 | 2/1978 | Lind ................................... 324/448 |
| 4,078,211 | 3/1978 | Longman ....................... 324/71 CP |
| 4,208,256 | 6/1980 | Inoue ............................... 204/129.2 |

FOREIGN PATENT DOCUMENTS

| | | |
|---|---|---|
| 966369 | 8/1964 | United Kingdom . |
| 1073461 | 6/1967 | United Kingdom . |
| 1174438 | 12/1969 | United Kingdom . |
| 1195562 | 6/1970 | United Kingdom . |
| 1218200 | 1/1971 | United Kingdom . |
| 1256291 | 12/1971 | United Kingdom . |
| 1485750 | 9/1977 | United Kingdom . |
| 1558132 | 12/1979 | United Kingdom . |
| 1558507 | 1/1980 | United Kingdom . |

Primary Examiner—Michael J. Tokar
Attorney, Agent, or Firm—Cushman, Darby & Cushman

[57] ABSTRACT

Methods and apparatus for monitoring the condition of dielectric fluid used in EDM are described. A continuous sample of dielectric liquid is withdrawn from a tank containing the EDM electrode and workpiece and is passed between electrodes of a capacitance cell before being returned to the tank. The capacitance between the electrodes gives an indication of the amount of metal particles resulting from EDM in the dielectric liquid. In another arrangement a magnetic field is used to direct most ferrous particles through a capacitance cell or part of a capacitance cell while most non-ferrous particles pass through another cell or another part of the cell. Measurement of the capacities of the cells or parts of cells provides an indication of the relative amounts of ferrous and non-ferrous particles in the dielectric liquid. The relative concentrations of particles of different sizes can be measured by passing the sample dielectric through a number of cells with each cell having a different pore-size filter at its inlet. The capacitance of each cell then indicates the amount of particles within a predetermined range in the dielectric liquid.

15 Claims, 7 Drawing Figures

METHODS AND APPARATUS FOR MONITORING THE CONDITION OF DIELECTRIC LIQUID IN ELECTRIC DISCHARGE MACHINING

The present invention relates to methods and apparatus for monitoring the condition of dielectric liquid used in electrical discharge machining (EDM) alternatively known as spark erosion.

In EDM an electrode and a workpiece are immersed in a dielectric liquid and separated from one another by a small gap. Current pulses are applied through the gap as discharges occur in the form of a number of sparks. These discharges remove metal from the workpiece and also to some extent from the electrode. The currents passed through the gap, the durations of voltage pulses causing the currents to flow and the size of the gap are initially set according to a number of factors including the type of materials used and the workpiece finish required. These settings are changed as machining progresses, particularly with a view to giving the workpiece an acceptable finish.

A major factor in choice of these variables as machining progresses is the amount of contamination in the dielectric liquid caused by suspended particles removed from the workpiece and the electrode. Further after a time it is necessary to replace the contaminated dielectric liquid with clean liquid.

The object of the present invention is to provide an economic way of monitoring the condition of the dielectric liquid. In some embodiments the invention also allows surface finish to be monitored.

According to a first aspect of the present invention there is provided a method of monitoring the condition of dielectric liquid used in an electrical discharge machining process, comprising passing, between two electrodes, at least a portion of the dielectric liquid used in an electrical discharge machining process, and, at least from time to time, deriving a signal representative of at least one component of the impedance across the electrodes or representative of change in at least one such component.

The components of the said impedance are the capacitance, resistance and inductance thereof.

Clearly the advantage of the method according to the invention is that the signal representative of the component of impedance, or change therein, provides an indication of the concentration of metal particles in the dielectric liquid, or of change in the said concentration.

According to a second aspect of the present invention there is provided apparatus for monitoring the condition of dielectric liquid used in electrical discharge machining apparatus, comprising a cell defining a passage for liquid between two electrodes, circulating means for circulating at least a portion of dielectric liquid being used in an electrical discharge machining process through the cell, and means for deriving signals representative of at least one component of the impedance across the electrodes or representative of change in at least one such component.

An EDM machine may include the monitoring apparatus of the preceding paragraph.

The cell may comprises a hollow cylindrical chamber containing a hollow cylindrical intermediate electrode which surrounds a cylindrical central electrode, the three cylinders preferably being coaxial with one another. The chamber wall may be made of conducting material and may be connected by a first connection to the central electrode while a second connection is provided for the intermediate electrode. The capacitance between the first and second connections may be measured, in operation, to provide an indication of the amount of machining debris in the dielectric liquid.

In order to monitor ferrous particles removed from a workpiece at the same time as monitoring non-ferrous particles removed from an EDM electrode, means for providing a magnetic field may be used to cause most ferrous particles to pass between one pair of electrodes or into one cell while most non-ferrous particles pass between another pair of electrodes or into another cell. For example if the two electrode pairs have a common electrode the cell having an intermediate electrode may be used. Magnets may then be fixed to the outside of the cell with the result that most ferrous particles pass between the intermediate electrode and the chamber wall while most non-ferrous particles pass between the central electrode and the intermediate electrode. In this case a separate connection is provided for the central electrode so that the capacitance between the central electrode and the intermediate electrode can be measured separately from, or compared with, the capacitance between the intermediate electrode and the chamber wall.

In order to provide an indication of the concentrations of particles of different sizes in the dielectric fluid, a number of capacitance cells, each of which may be as outlined above, may be connected in parallel to receive liquid circulated from the said tank. Each cell has a respective filter at its input and the maximum size of particle which each filter passes is different for each cell. In this way the capacitance or change in capacitance of each cell provides an indication of the concentration or a change in concentration, respectively, of particles within a certain size range occurring in the dielectric fluid.

In order to provide an indication of the size of particles in the dielectric fluid, the cell of the second aspect of the invention may contain a plurality of pairs of electrodes, one pair being formed by the said two electrodes, and the electrodes of the pairs being spaced from each other by precise but different distances. Alternatively a plurality of cells with pairs of electrodes spaced at different distances may be used. The resistance across the pairs of electrodes is measured and the occurrence of intermittent short circuits between electrodes of one pair indicates that the dielectric liquid contains particles approximately equal to the distance between the electrodes of that pair.

Since the temperature of the dielectric affects the capacitance of the cell, means are either provided for maintaining the temperature in the cell constant, regardless of the temperature of the dielectric pumped at the workpiece area, or means provided for measuring capacitance or changes in capacitance include means for automatically compensating for temperature.

According to a third aspect of the invention there is provided apparatus for monitoring the condition of dielectric liquid used in electrical discharge machining comprising a pair of electrodes which, in operation are immersed in a tank of dielectric liquid, an electrical supply for applying a voltage between the electrodes which is just greater than the voltage which causes breakdown between the electrodes when the dielectric liquid is not significantly contaminated, means for detecting discharges between the electrodes and means for reducing the voltage applied between the electrodes by a predetermined decrement when a discharge is detected, the said tank also containing, in operation, a workpiece and a further electrode, in close proximity thereto, for machining the workpiece, and the applied voltage providing an indication of contamination of the dielectric liquid.

Preferably in both the methods and apparatus of the invention, the portion of dielectric liquid passed between the electrodes is drawn from the immediate region of the EDM gap.

Figure 2A:
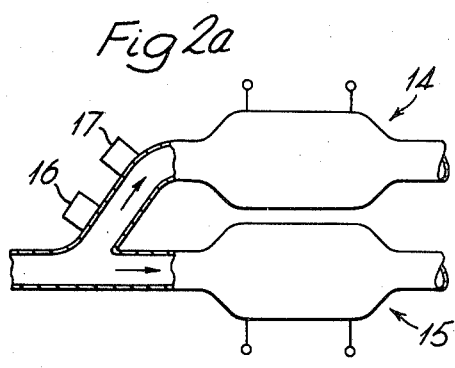
Figure 2B:
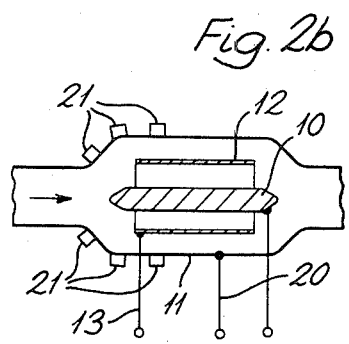
Figure 3:
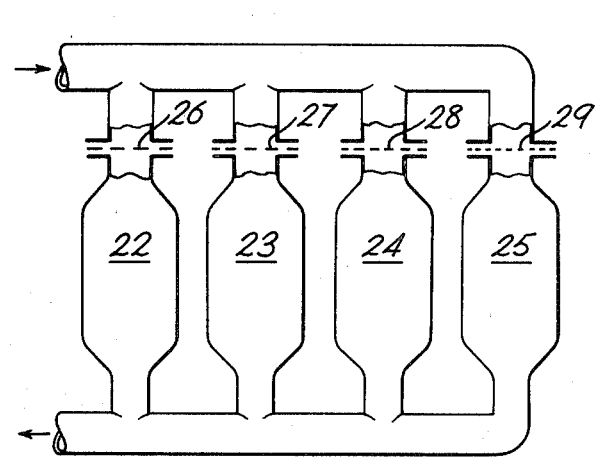

Certain embodiments of the invention will now be described by way of example with reference to the accompanying drawings, in which:

FIG. 1 is a schematic cross-section of a capacitance cell for use in apparatus according to the second aspect of the invention, FIGS. 2(a) and 2(b) are schematic diagrams of cell arrangements for use in indicating the proportions of ferrous and non-ferrous particles in dielectric liquid, FIG. 3 is a schematic diagram of a cell arrangement for indicating the relative proportions of particles of different sizes in dielectric fluid.

Figure 4:
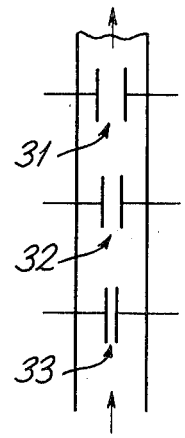
Figure 5:
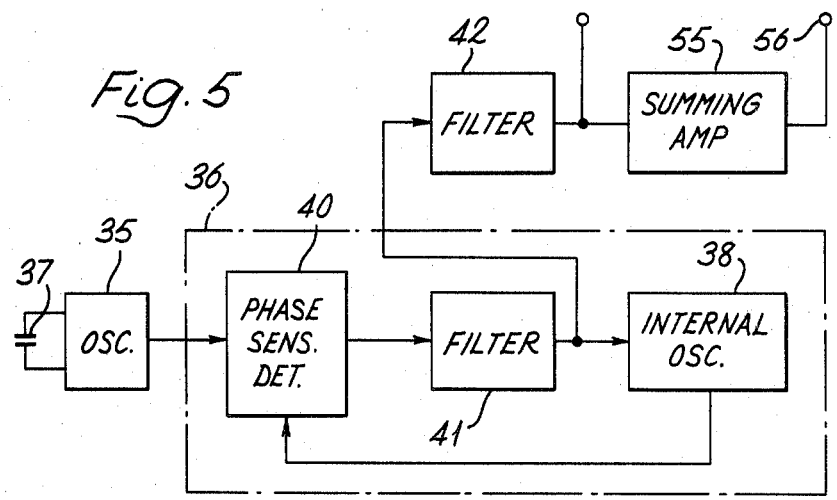
Figure 6:
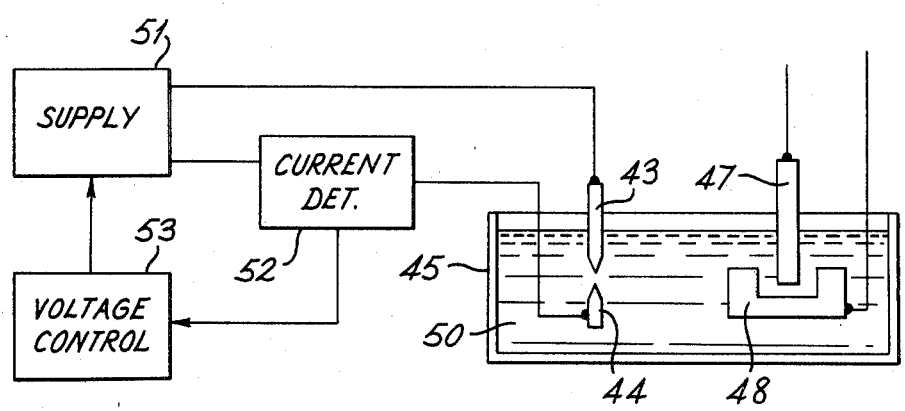

FIG. 4 is a schematic diagram of a cell arrangement for indicating the size of particles in dielectric fluid, FIG. 5 is a block diagram of means for providing an output representative of the capacity of a capacitance cell, and FIG. 6 is a schematic diagram of apparatus according to the third aspect of the invention.

In FIG. 1 a capacitance cell has a solid cylindrical centre electrode 10 connected to an outer electrode formed by the cell wall 11. Between the centre electrode and the outer casing is a hollow cylindrical intermediate electrode 12 with a connection 13 which passes through, and is insulated from, the cell casing.

A dielectric liquid sample from the tank of an EDM machine is continuously withdrawn from the region of the electrode and workpiece by means of a tube. The cell of FIG. 1 is connected to the tube and liquid sample from the cell passes by way of a pump 19 back to the tank. Thus in operation the pump continuously circulates a sample of the dielectric liquid through the cell. Preferably the cell and the pump are arranged to provide streamlined flow through the cell. In this and the other drawings the direction of fluid flow is indicated by one or more arrows.

The electrical capacitance of the cell of FIG. 1 is connected by means of the two connections shown as part of an oscillator 35 (see FIG. 5) operating, for example, in the range 30 to 70 KHz. The oscillator 35 has its output connected to an integrated circuit 36 (indicated by a dashed line) of the type used in forming a phase-locked loop (PLL). The capacitance of the cell (which is designated 37 in FIG. 5) when filled with clean dielectric liquid is known and with this capacity the oscillation frequency is the same as that of an internal oscillator 38 in the PLL circuit. The internal oscillator 38 has an output connected to a phase sensitive detector 40 which also receives a signal from the oscillator 35. After being passed through a filter 41, the variable voltage at the output of the phase sensitive detector 40 is used to control the frequency of the internal oscillator 38 and to provide an output voltage. The output voltage from the PLL circuit is inversely proportional to frequency and therefore proportional to the capacity of the cell. Since the output voltage from the PLL circuit 41 contains high frequency components it is passed through a low pass filter 42 having a cut-off at about 40 Hz. Thus change in the amount of debris in the dielectric liquid changes the oscillator frequency and causes the output of the PLL circuit to provide a voltage proportional to the new capacity of the cell.

Alternatively cell capacitance may be measured in any suitable known way as often as is required to provide an indication of the amount of metal particles in the liquid sample.

If an indication of change in capacity is required, the voltage from the filter 42 may be biassed to zero, when the dielectric liquid is clean, for example using a summing amplifier 55 with an appropriate biassing voltage, and changes in capacity are then indicated by the output voltage at a terminal 56.

In one example of the measuring circuit the oscillator 35 may be a type 555 integrated circuit which is a timer circuit capable of generating a square wave, the PLL integrated circuit 36 may be type 4046, the filter 42 may be constructed around a type TL081 amplifier, and the summing amplifier 55 may be a 741 operational amplifier. A suitable value for the capacitance of the cell of FIG. 1 is 120 pF and the oscillator frequency may then be about 100 kHz.

The capacitance of the cell or the change in capacitance thereof provides an indication of the amount of material removal from the workpiece, and so gives guidance as to when the dielectric liquid should be changed or how to adjust its flow velocity. In addition an indication of the amount of particles in the dielectric liquid allows machining conditions such as the size of the gap between the electrode and the workpiece, and the voltage applied to the workpiece to be adjusted in accordance with the changed properties of the dielectric liquid.

In order to obtain a suitable capacity the gaps between the intermediate electrode 12 and the central electrode 10 and between the electrode 12 and the outer wall 11 may be about 25 mm. In some cases it is useful to employ two cells, each as shown in FIG. 1, with the liquid passing in series through the cells. The capacitances of the two cells are then connected in parallel in the oscillator circuit mentioned above.

In order to prevent metal particles forming short circuits if such particles bridge the gaps between the electrodes, the metal surfaces of the electrodes are, advantageously, coated with Shellac or another insulating coating.

FIGS. 2(a) and 2(b) show different cell arrangements for distinguishing between the amount of ferrous and non-ferrous debris in the dielectric liquid. Such arrangements are useful in assessing the relative wear of a non-ferrous electrode and a ferrous workpiece used in an EDM process. As before a continuous sample of liquid is withdrawn from the tank containing the electrode and the workpiece and returned thereto after passing through the cell arrangement.

In FIG. 2(a) first and second cells 14 and 15 are each of the same form as the cells shown in FIG. 1. The cell 15 is in line with the general flow of fluid coming from the tank and is below the cell 14 so that particles in suspension tend to pass through the cell 15. However magnets 16 and 17 are positioned at a junction 18 in the tube from the tank, where the tube walls are constructed from non-magnetic material, with the result that most ferrous particles pass into the cell 14 while most non-ferrous particles continue through the cell 15. Hence measurement of the relative capacitances of the cells 14 and 15 give indications of the amount of ferrous and non-ferrous particles, respectively, in the dielectric fluid. The outlets of the cells 14 and 15 are connected together at a further junction (not shown) and this junction is connected to the tank to allow dielectric liquid to pass back into the tank by way of a filter.

A similar approach is shown in FIG. 2(b) except that only a single cell is used, this cell being of the type shown in FIG. 1 except that the connection to the central conductor 10 is insulated from the cell wall 11 which has a separate connection 20 and the cell walls must be substantially non-magnetic instead of being optionally non-magnetic. In addition magnets 21 cause most ferrous particles to pass between the intermediate electrode 12 and the outer wall 11 of the cell while most non-ferrous particles pass between the intermediate electrode and the central electrode 10 since these particles take the most direct route between the cell inlet and outlet. Measurement of the capacitances obtained between the inner electrode 10 and the intermediate electrode 12, and between the intermediate electrode 12 and the cell wall 11 provide indications of the amount of non-ferrous and ferrous particles, respectively, in the dielectric fluid.

In order to provide an indication of particle sizes in the dielectric and therefore obtain an indication of the surface finish of the workpiece the embodiment of FIG. 3 may be used. Four cells 22 to 25 are shown by way of example and each may be as shown in FIG. 1. The cells are connected in parallel in the path for liquid samples withdrawn from the dielectric tank and returned thereto. Four different removable standard pore-size filters 26 to 29 are positioned at the respective inlets to the cells 22 to 25. Hence the capacities of the cells provide indications of the amounts of particles of different sizes in the dielectric fluid. In EDM as the final shape and size of the workpiece is approached it is customary to reduce the current passing through the machining gap which in turn reduces the particle size and provides an improved workpiece surface. Thus in the course of machining, as the current passing through the gap is reduced, the capacity of cell 22 first falls and is then followed by the capacities of the other cells 23, 24 and 25 falling in succession so that when the cell 25 reaches a predetermined capacity, it is an indication that the workpiece finish has reached a required standard. The variation of the various capacities shows how the EDM process is progressing and the amounts of material removed.

In order to give information on particle size, the arrangement shown schematically in FIG. 4 may be used. A cell having three pairs of electrodes 31, 32 and 33 is connected to receive a continuously circulated sample of dielectric liquid. Each pair of electrodes is separated by a different precise gap and the size of particles in the dielectric is detected by measuring the resistance across the pairs of electrodes. For example when the dielectric contains large particles all three pairs of electrodes will be intermittently short-circuited while when the particles are smaller only the pairs 32 and 33 will be short-circuited. Thus particle size which is related to the finish of the workpiece is monitored. The electrodes are shown schematically only in FIG. 4, and they need not, of course, be planar.

In a further embodiment of the invention shown in FIG. 6 electrodes 43 and 44 are immersed directly in a tank 45 which contains an EDM electrode 47 and a workpiece 48. The breakdown voltage of a dielectric liquid 50 in the tank 45 is then continuously monitored as follows: a voltage from a supply 51 is applied between the electrodes 43 and 44, the voltage being just below the breakdown voltage of the pure dielectric liquid. As machining takes place and the liquid accumulates impurities its dielectric strength falls causing breakdown which is detected by a current detector circuit 52 to occur. The voltage from the supply 51 is then reduced by a voltage control circuit 53 and a signal representing the new applied voltage is supplied to the EDM machine for use in controlling the gap voltage. This arrangement is particularly useful in adaptive EDM machines.

While a number of specific embodiments of the invention have been described it will be clear that the invention can be put into practice in many other ways. For example other configurations of electrodes may be used, the electrodes may be positioned in relation to the workpiece in other ways, other impedance components may be measured and other circuits may be used for this purpose or for measuring change in an impedance component. Also the permanent magnets of FIGS. 2(a) and 2(b) may be repositioned and/or replaced by electromagnets with equivalent or different magnetic fields.

We claim:

1. A method of monitoring the condition of dielectric liquid being used in an electrical discharge machining process, comprising:
   causing at least a portion of the dielectric liquid used in an electrical discharge machining process to flow in contact with two adjacent but separated electrodes, and
   at least from time to time, deriving a signal representative of change in at least one component of the impedance across the electrodes due to change in condition of said liquid.

2. Electrical discharge machining apparatus including means for monitoring the condition of dielectric liquid used in electrical discharge machining apparatus, comprising:
   a cell defining a passage for liquid to flow in contact with two adjacent but separated electrodes,
   circulating means for circulating at least a portion of dielectric liquid being used in an electrical discharge machining process through the cell, and
   means for deriving, while machining is taking place, signals representative of change in at least one component of the impedance across the electrodes due to change in condition of said liquid.

3. Apparatus according to claim 2 wherein the cell comprises a hollow cylindrical chamber forming one electrode and containing a hollow cylindrical intermediate electrode which surrounds a cylindrical central electrode, the three cylinders being coaxial with one another, and the said two electrodes being selected from the following arrangements:
   any two of the said electrodes,
   any two of the said electrodes connected to form a single electrode, and
   the other said electrode.

4. Apparatus according to claim 2 including means for providing a magnetic field such that ferrous particles tend to pass along one of two paths, said one path being between the said electrodes and the other said path avoiding passage between said electrodes, non-ferrous particles tending, in operation, to pass along the said other path.

5. Apparatus according to claim 2 including a further pair of separated electrodes in the said cell, the spacings between the electrode pairs providing parallel paths for the dielectric liquid, and means for providing a magnetic field such that most ferrous particles in the dielectric pass between one pair of electrodes and most non-ferrous particles pass between the other pair of electrodes.

6. Apparatus according to claim 2 including at least one further cell, the cells being connected to provide respective parallel paths for the dielectric liquid sample, and a number of filters, one for each cell and located at the inlet thereto, each filter passing particles in a size range which is different from that of the other filter or filters, and an electrode arrangement which allows said signal deriving means to derive respective signals for each cell.

7. Apparatus according to claim 2 wherein the cell contains at least one further pair of separated electrodes, the electrodes of each pair are positioned opposite one another with a passage for dielectric liquid between the electrodes of that pair, and the spacings between the electrodes of each pair differ from pair to pair.

8. Apparatus according to claim 2 wherein signals representative of change in capacity, between the electrodes are derived by the means for deriving signals.

9. Apparatus according to claim 8 wherein the means for deriving signals comprises an oscillator which includes the capacity between the electrodes and which has an oscillation frequency dependent on the said capacity, and a phase-locked-loop circuit with an input terminal connected to receive signals from the oscillator and an output terminal at which a voltage representative of the said oscillation frequency appears.

10. A method according to claim 1 wherein change in one component of the impedance across the electrodes is indicated by a change in a signal representing one component of the impedance across the electrodes.

11. Electrical discharge machining apparatus according to claim 2 wherein the means for deriving signals representative of change in at least one component of the impedance across the electrodes is constructed to provide an indication of successive values of the said impedance.

12. A method of monitoring the condition of dielectric liquid being used in an electrical discharge machining process, comprising:

causing at least a portion of the dielectric liquid used in an electrical discharge machining process to flow in contact with two adjacent but separated electrodes, and, at least from time to time, deriving a signal representative of at least one component of the impedance across the electrodes, the said component being dependent on the condition of the said liquid.

13. Electrical discharge machining apparatus including means for monitoring the condition of dielectric liquid used in electrical discharge machining apparatus, comprising:

a cell defining a passage for liquid to flow in contact with two adjacent but separated electrodes, circulating means for circulating at least a portion of dielectric liquid being used in an electrical discharge machining process through the cell, and means for deriving, while machining is taking place, signals representative of at least one component of the impedance across the electrodes, the said component being dependent on the condition of the said liquid.

14. Apparatus according to claim 2 or 13 including a further cell, the cells providing parallel paths for the dielectric liquid, and means for providing a magnetic field such that most ferrous particles pass to one cell and most non-ferrous particles pass to the other cell.

15. Electrical discharge machining apparatus comprising:

a tank which, in operation, contains a workpiece, a primary electrode, a first electrical supply for applying voltage between a workpiece and the primary electrode such that electrical discharge machining of the workpiece by discharges from the electrode takes place, a pair of secondary electrodes located, at least in operation, in the tank, a second electrical supply for applying a voltage between the secondary electrodes which is just smaller than the voltage which causes breakdown between the electrodes when the dielectric liquid is not significantly contaminated, discharge-detection means for detecting discharges between the secondary electrodes, and voltage control means, coupled to the discharge-detection means, for reducing the voltage applied between the secondary electrodes by a predetermined decrement when a discharge is detected as indicated by the discharge-detection means, the voltage applied between the secondary electrodes providing an indication of contamination of the dielectric liquid.

* * * * *